United States Patent [19]

Croset et al.

[11] Patent Number: 4,741,817
[45] Date of Patent: May 3, 1988

[54] ELECTROCHEMICAL SENSOR FOR THE CONCENTRATION OF ASPECTS IN A FLUID MIXTURE AND SYSTEM FOR REGULATING THE RICHNESS OF AN AIR-FUEL MIXTURE UTILIZING SUCH A SENSOR

[75] Inventors: Michel Croset; Noël Nouailles; Joël Perret; Jean-Philippe Schnell; Gonzalo Velasco, all of Paris, France

[73] Assignee: Socapex, Suresnes, France

[21] Appl. No.: 716,618

[22] Filed: Mar. 28, 1985

Related U.S. Application Data

[63] Continuation of Ser. No. 318,800, Nov. 6, 1981, abandoned.

[30] Foreign Application Priority Data

Nov. 17, 1980 [FR] France ............................ 80 24380

[51] Int. Cl.$^4$ .................................. G01N 27/46
[52] U.S. Cl. .................................. 204/425; 204/1 T; 204/426; 204/427; 204/429
[58] Field of Search .................. 204/1 S, 421–429

[56] References Cited

U.S. PATENT DOCUMENTS

| | | | |
|---|---|---|---|
| 3,768,259 | 10/1973 | Carnahan et al. | 204/195 S |
| 3,907,657 | 9/1975 | Heijne et al. | 204/1 S |
| 3,909,384 | 9/1975 | Jasinski et al. | 204/195 S |
| 3,923,624 | 12/1975 | Beekmans et al. | 204/195 S |
| 4,032,285 | 6/1977 | Rohr et al. | 431/12 |
| 4,158,166 | 6/1979 | Isenberg | 324/439 |
| 4,224,113 | 9/1980 | Kimura et al. | 204/195 S |
| 4,226,692 | 10/1980 | Isenberg | 204/195 S |
| 4,248,941 | 2/1981 | Louis et al. | 204/195 S |
| 4,271,000 | 6/1981 | Croset et al. | 204/195 S |
| 4,272,329 | 6/1981 | Hetrick et al. | 204/195 S |
| 4,272,350 | 6/1981 | Croset et al. | 204/195 S |
| 4,277,323 | 7/1981 | Muller et al. | 204/195 S |
| 4,292,158 | 9/1981 | Muller et al. | 204/195 S |
| 4,298,573 | 11/1981 | Fujishiro | 204/425 |
| 4,306,957 | 12/1981 | Ishitani et al. | 204/195 S |
| 4,334,510 | 6/1982 | Croset et al. | 204/195 S |
| 4,337,746 | 7/1982 | Masaki | 204/195 S |
| 4,384,935 | 5/1983 | De Jong | 204/425 |

FOREIGN PATENT DOCUMENTS

| | | |
|---|---|---|
| 0012647 | 6/1980 | European Pat. Off. . |
| 2051855 | 4/1971 | France . |
| 2223695 | 10/1974 | France . |
| 2440552 | 5/1980 | France . |
| 2056083A | 3/1981 | United Kingdom ............ 204/424 |

OTHER PUBLICATIONS

"Oxygen Sensors", by T. Takeuchi.

*Primary Examiner*—T. Tung
*Attorney, Agent, or Firm*—Cushman, Darby & Cushman

[57] ABSTRACT

Electrochemical sensor for the concentrations of species in a fluid mixture comprising a measuring cell of the type having a partial pressure internal reference electrode incorporating a catalysis region in which the gaseous mixture is brought into thermodynamic equilibrium and functioning according to the so-called "assay" process, so that only a small quantity of the gaseous mixture to be analyzed is admitted into the sensor. It also comprises a supplementary cell functioning as an ionic pump, so as to continuously modify the composition of the gaseous mixture admitted into the sensor under the control of a regulatable electric current.

21 Claims, 8 Drawing Sheets

ELECTROCHEMICAL SENSOR FOR THE CONCENTRATION OF ASPECTS IN A FLUID MIXTURE AND SYSTEM FOR REGULATING THE RICHNESS OF AN AIR-FUEL MIXTURE UTILIZING SUCH A SENSOR

This is a continuation of application Ser. No. 318,800, filed Nov. 6, 1981, which was abandoned upon the filing hereof.

BACKGROUND OF THE INVENTION

The present invention relates to electrochemical sensors for the concentrations of species in a fluid mixture and in particular to a system for regulating the richness of an air-fuel gaseous mixture.

One well known type of electrochemical sensor operates on the principle of a concentration cell and the measurement of the partial pressure of one or more species of the gaseous mixture to be analysed. The gaseous mixture which is present in a first compartment, for example an oxygen-inert gas mixture, is separated from a reference medium by the wall of a solid electrolyte, whereof each face carries an electrode. As is known, the equations governing these sensors are:

at the electrode/electrolyte interfaces:

(1)

The voltage $V_{E1/E2}$ which then develops between the electrodes is given by the NERNST law:

$$V_{E1/E2} = \frac{RT}{4F} \ln \frac{P_1}{P_2} \quad (2)$$

with

R=constant of perfect gases=8.314 (mole. °K.)
F=Faraday number=96,490 C
T=absolute temperature in degrees Kelvin
$P_1$ and $P_2$=partial pressures of 1 and 2 in compartments 1 and 2.

In the case where the mixture is reactive, e.g. a mixture of $O_2$ and CO and if the electrode is a catalyst of the reaction of these gases, the following reaction occurs:

$$2CO + O_2 \rightleftharpoons 2CO_2 \quad (3)$$

and finally if combustion is complete up to the time of achieving the reversible thermodynamic equilibrium the following relation is proved:

(4)

with K(T) a temperature-dependent equilibrium coefficient and $CO|O_2|^{\frac{1}{2}}$, $CO_2$ the partial pressures of carbon monoxide, oxygen and carbon dioxide.

Recent approaches in connection with the construction of sensors propose the use of a means combining the electrode function and the reference medium function. For this purpose, an electrode base on a combination of the following type is used: M-MX in which M is a metal and X oxygen or a halogen to be detected (e.g. M-MO in the case of the detection of oxygen). As an improvement to this approach, sensors have also been proposed which are based on the method of thin layers used in microelectronics. These two construction types, among others, make it possible to in part overcome the parasitic effects of temperature on the response curve of the sensors. Thus, on the basis of equations (3) and (4) the value of $V_{E1/E2}$ is doubly dependent on the "temperature" parameter. Thus, an appropriate choice on the basis of the formation heat tables of M-MX makes it possible to partly compensate the two temperature-sensitive terms.

The invention relates to sensors of the type comprising electrodes or other means placed upstream of the electrochemical measuring cell carrying out complete catalysis, in such a way that the gaseous mixture to be analysed reaches thermodynamic equilibrium at least at the level of the electrode-electrolyte interface and whereof one of the electrodes is of the type described hereinbefore on the basis of a combination M-MX.

Such sensors are used in regulating internal combustion engines and particularly for regulating the admission of the air-fuel mixture to the carburettor or the fuel injector. The sensor is then placed in the exhaust circuit and analyses the relative concentration of the oxygen and carbon monoxide contained in the gas. The sensor must then be adapted to certain characteristics specific to this use. Thus, the exhaust gas arrives in jerks with the timing of the alternating movement of the different pistons. These problems are solved by taking samples of the gas to be analysed and only these are introduced into the sensor where they are brought into thermodynamic equilibrium. The term "assay" is used and if they are sufficiently close together there is a tendency towards a continuous analysis, although in reality the sensor functions under dynamic conditions. To arrive at this result, means are generally positioned upstream of the sensor which selectively decelerate the gas passing through them and which limit the gaseous exchange between the external medium and the interior of the sensor. By analogy with the laws governing electric circuits these means can be called "transfer impedance means". Various solutions have been proposed and they are based on two approaches. According to the first approach, the gaseous mixture to be analysed enters the sensor by one or more metering holes. According to the second approach, the gaseous mixture traverses a porous solid material, this being generally the case with sensors having a planar structure produced by the thin layer principle. The porous material may also coincide with the extension of the measuring electrode. According to a particularly advantageous variant of this prior art sensor, the electrode is in the form of a layer of porous catalyst material and the gas to be analysed propagates within the same in a direction parallel to the largest dimensions of the electrode before reaching the actual measuring area. Such a sensor is described in U.S. Pat. No. 4,271,000.

The sensors, whose operation and characteristic principles have been described hereinbefore, have response curves which exhibit a sudden dip when the stoichiometry of the gaseous mixture to be analysed is reached. Moreover, the response of these sensors consists of a set of curves and not a single curve and said set is parametrized in temperature due to the aforementioned dependence and essentially coincide in the dip region. Therefore, it is usually possible to use this part of the response curves and consequently it is only possible to reliably and repetitively detect the stoichiometry of the reaction defined by relation (3).

These sensors can be used as they are in certain countries, particularly countries imposing severe anti-pollution regulations. The motor then operates with a stoichiometric air-fuel mixture.

Other countries, such as certain of the European countries, impose a lean mixture, particularly as a result of fuel economy measures. Thus, the prior art sensors with an "all or nothing" response curve for a single regulating point cannot be used for this type of operation. To solve this problem and more generally modify the regulation point two approaches have been proposed.

According to the first approach, it is possible to partly linearize the response curve by modifying certain components of the sensors, particularly by adopting a special measuring electrode construction. Such sensors are described in European Patent Application EP-A-0018871, published on November 12, 1980. The device described therein is sensitive to carbon monoxide and not to oxygen. This is advantageous because the carbon monoxide content variation dynamics are generally greater than that for oxygen in the exhaust gases. However, this device can only be used in a restricted range of relative concentrations directly beyond which parasitic effects of temperature become too great for ensuring an adequate measuring precision.

According to the second approach, "the transfer impedance" as defined hereinbefore is made selective by the use of a porous material especially adapted to the fluid to be analysed.

Thus, in the case of a gaseous mixture of two species, for example oxygen and carbon monoxide, one of the species can diffuse more rapidly than the other within the porous material in question. In other words, to a given mixture composition on entering the sensor, may correspond a different mixture composition within the porous material and then at the measuring electrode.

By integrating into the sensor a predetermined selective transfer impedance associated with catalysis means for bringing the gaseous mixture into thermodynamic equilibrium prior to analysis, the apparent concentration of the species of a gaseous mixture is measured, i.e. that at the measuring electrode and consequently the regulation point is displaced on either side of the stoichiometry of the gaseous mixture which in actual fact circulates in the exhaust pipes.

A regulating system using this type of sensor described in European Patent Application No. 0 0115 30, published on May 28, 1980, is less dependent on the temperature effects because in this case detection also takes place of the dip in the response curve and which occurs on either side of the stoichiometry as a function of the nature of the "transfer impedance", i.e. in a region of the curve which is less sensitive to this parameter. However, the displacement amplitude permitted by these devices is relatively limited and is fixed once and for all at a predetermined value at the time of manufacture.

In certain applications, particularly in systems for regulating the richness of the air-fuel mixture, entering the cylinders of an internal combustion engine controlled by a digital or analog computer, it is necessary to be able to develop the regulation point as a function of parameters measured by different sensors, such as the temperature or speed of the vehicle driven by the engine and this takes place in a continuous manner in accordance with predetermined laws or laws produced by the computer.

BRIEF SUMMARY OF THE INVENTION

The prior art sensors cannot be used for such operating modes. The invention aims at obviating this disadvantage by proposing a sensor construction integrating a member of the ionic pump type making it possible to continuously develop the apparent relative concentration measured at the measuring electrode by means of an electronic control current.

This type of member is used in the prior art for regulating the concentration of a chemical species in an enclosure or pipe, e.g. oxygen, by carrying out a reversible pumping of the species contained in a second reservoir enclosure.

An ionic pump is generally constructed like an electrochemical cell. A diaphragm constituted by a solid electrolyte, which is permeable to the ions of the chemical species to be "pumped" has on its two faces electrodes connected to the terminals of an electronic current source. As a function of the amplitude and polarity of the current, an ionic current is produced within the electrolyte and as a result there is a transfer of ions from the species which recombine on one of the two electrodes, as a function of the conduction direction. In the case of oxygen, the aforementioned relation (1) is satisfactory.

An example of an ionic pump is described in the article of FOULETIER et al "Measurement and regulation of oxygen content in gases using solid electrolyte cells, III oxygen pump-gauge", which appeared in the British "Journal of Applied Electrochemistry", No. 5, 1975, pp. 111 to 120.

The present invention therefore relates to an electrochemical sensor for the concentrations of reactive species contained in a fluid mixture of the type comprising a first region having means for limiting the fluid flow introduced into a second region having catalysis means for bringing the admitted fluid into thermodynamic equilibrium and a third region having an electrochemical measuring cell for the detection of the stoichiometry of the reaction of the said reactive species and comprising at least one supplementary electrochemical cell incorporating a solid electrolyte which is an ionic conductor of one of the reactive species between the first and second electricity-conducting electrodes which are to be connected to an electric power supply so as to establish ionic conduction of the reactive species within the solid electrolyte of predetermined amplitude and polarity, the first electrode being in contact with a medium supplying or receiving the reactive species or one of its components and the second electrode being linked with the second region so as to modify the relative concentrations of the fluid admitted into the said region by extraction or injection of the reactive species in a quantity proportional to the predetermined amplitude.

The invention also relates to a system for regulating the richness or concentration of an air-fuel gaseous mixture utilizing such a sensor.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
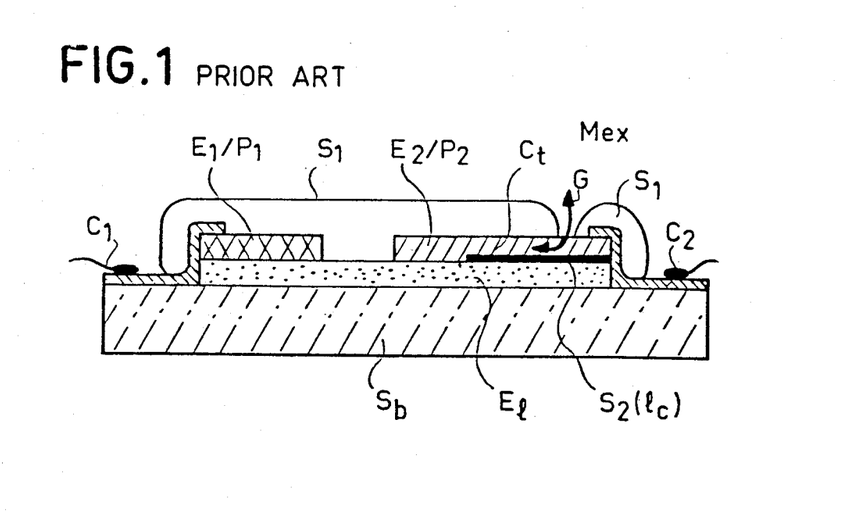
FIGS. 1 and 2 an example of a prior art sensor and its operation.

FIG. 1 describes a prior art sensor structure which simultaneously incorporates the "assay", catalysis and measurement functions performed by thin or thick layer deposition processes. For the purposes of the following description, it is assumed that the electrochemical sensors are intended for use in the detection of relative concentrations of oxygen and carbon monoxide, without this in any way limiting the scope of the invention. The main features of such a sensor will be defined hereinafter in connection with the illustration of the prior art.

The sensor of FIG. 1 comprises two electrodes deposited on a solid electrolyte $E_l$, itself deposited on substrate Sb. Electrodes $E_1/P_1$ and $E_2$ are located in the same plane. Electrode $E_1/P_1$ combines the functions of electrode and reference medium. Electrode $E_1/P_1$ is also protected from the external medium by a tight, inert insulant $S_1$ which covers it. A combination of the type Ni/NiO can be used for producing the electrode—reference medium. Electrode $E_2$ has two regions and is directly connected by an opening made in insulating body $S_1$, which also covers it, with the medium to be analysed Mex in which circulates the gaseous medium G. In the first region Ct, the electrode is insulated at its lower face from electrolyte $E_1$ by an insulating medium $S_2$ of the same type as $S_1$ over a length $l_c$. The fluid to be analysed must pass through body Ct, which is a catalyst. In this region, the reactive species of the mixture to be analysed (e.g. CO and $O_2$ in the case of exhaust gases) are brought into complete thermodynamic equilibrium before reaching the electrochemical cell: $[E_2/P_2-E_l-E_1/P_1]P_2$ constitutes the real medium to be analysed. In a practical embodiment, region Ct is only the extension of electrode $E_2/P_2$ and is made from the same material, e.g. platinum deposited in thin layer form. Catalysis takes place by the fluid passing through the catalyst in a direction parallel to the plane of the electrodes. The electrodes are extended outwards by metallic connections to which can be welded contacts $C_1$ and $C_2$, said connections being e.g. in the form of platinum varnish. Substrate $S_b$ can be made from a good insulant at the operating temperature of the device (e.g. corundum) and ensures the mechanical behaviour of the assembly. This substrate can be extended in a random direction for adaptation to means for fixing to a box or case.

In a not illustrated variant, the solid electrolyte can be a thick plate and there is no substrate.

Typical values are:
length $l_c$: 0.1 to 0.5 mm
thickness of electrodes: 1000 Å at 100 $\mu$m
thickness of electrolyte: 1000 Å at 100 $\mu$m The deposits can be made by per se known methods such as vacuum deposition (cathodic sputtering, evaporation), vapour phase deposition, electrochemical deposition, ion implantation or a combination of two or more of these methods.

Figure 2:
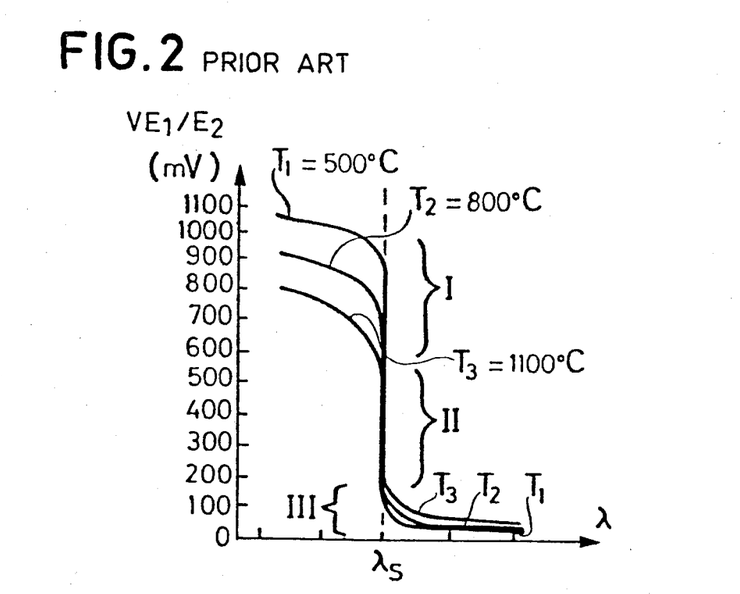

FIG. 2 illustrates a set of response curves for prior art sensors for the oxygen concentration of exhaust gases of an internal combustion engine. Each curve represents the interelectrode potential difference $V_{E1/E2}$ as a function of the oxygen concentration in the exhaust gas at constant temperature. Particular note should be made of the three regions, whereby in regions I and III the different curves are clearly differentiated from one another. Thus, on referring to the aforementioned relations (2) and (4) it can be seen that they contain in each case the parameter "absolute temperature T". It is therefore difficult to exploit these parts of the curves because the exhaust gases do not have a constant temperature. However, in region II of FIG. 2, corresponding to the dip, the various curves substantially coincide. Only this region is normally exploited. The output of the sensor is transmitted to a not shown electric control member, which detects the rapid dip of curve $V_{E1/E2}$ about abscissa point $\lambda_s$, representing the stoichiometric ratio of the mixture, as measured at the measuring electrode $E_1/P_1$. The dip point is fixed, even if as a result of the process described in European Patent Application No. 0 0115 30 referred to hereinbefore, it is possible to slightly displace this dip point on either side of the stoichiometry at the time of manufacturing the sensor.

The invention aims at overcoming this limitation. To this end, the structure of the sensor integrates a supplementary cell identical to measuring cell $E_1-E_l-E_2$ functioning as an ionic pump and which will subsequently be called an ionic pumping cell.

Figure 3:
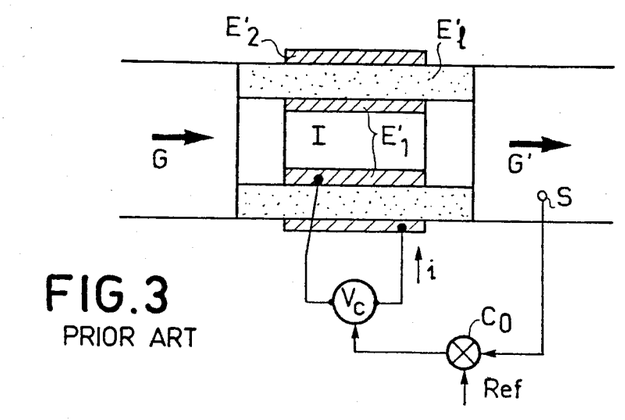
FIG. 3 diagrammatically an ionic pump.

Such an ionic pump is diagrammatically described in FIG. 3. It is substantially in the form of an electrochemical cell comprising a solid electrolyte $E'_l$ forming an ionic conductor of at least one given chemical species, e.g. oxygen and having an annular shape in the selected embodiment. A pair of electrodes, respectively $E'_1$ and $E'_2$ is deposited on both the inner and outer faces thereof. If a potential difference $V_c$ is applied between the electrodes, as a function of the amplitude and polarity, an ionic current is produced within the electrolyte, i.e. a transfer of ions from the species in question from electrode $E'_2$ to electrode $E'_1$ or vice versa, the amplitude of this ionic current being linked by a given law with the amplitude of the control voltage $V_c$. The electrodes must be porous or permeable to the given chemical species. Reference will be made hereinafter to the example of oxygen, bearing in mind that the oxygen can be either pure of included in a mixture of various fluids. The ionic current within the electrolyte is represented by an electronic current i in the electric circuit outside the cell. Current i can be deduced from the aforementioned relation (1).

The laws governing the operation of such ionic pump cells are known to the expert. However, it may be useful to refer to the following simplified relations and equations, it being assumed that the electronic conductivity of the electrolyte is negligible.

Firstly, the cell develops a counter-electromotive force $V_{E1/E2}$ given by the NERNST law and explained by relation (2).

The total weight in grams of the species transferred in ion form is given by the relation:

$$m = \frac{itM}{96\,490\,Z} \quad (4)$$

in which:
i is the electronic current
t the time in seconds
M the atomic mass of the species in question
Z the valence of the species.
For oxygen, the relation becomes:

$$m_o = \frac{8\,it}{96\,490} \quad (4a)$$

Current i can be obtained from the relation:

$$i = \frac{V_{E1/E2} + V_c}{Z\,\text{el}} \quad (5)$$

in which, besides $V_{E1/E2}$ and $V_c$ which have already been defined, $Z_{el}$ is the impedance of the solid electrolyte E'1 opposing the ionic conduction which, in a first approximation, is reduced to a resistance $R_{el}$ dependent on the dimensional characteristics of the solid electrolyte and its ionic conductivity at a given temperature.

By combining (5) and (1) we obtain:

$$i \cdot R_e = V_c + \frac{RT}{4F} \ln \frac{P_1}{P_2} \quad (6)$$

In the embodiment described relative to FIG. 3, $P_1$ and $P_2$ are the partial pressures respectively of media I and II, medium II can be considered as a reservoir medium containing at least oxygen and medium I the medium in which circulates a gaseous mixture, whose oxygen concentration must be controlled. In the present embodiment, a gaseous mixture G circulates in a pipe, passes through enclosure I constituted by the interior of the ionic pump and leaves in the form of a gaseous mixture G' with an oxygen concentration modified by the ionic pump. Generally, electrochemical measuring sensor S measuring the outlet concentration of mixture G' is positioned at the outlet. The electric signals are transmitted to a comparator Co receiving at a second input a reference value Ref in such a way that it acts on the control voltage $V_c$ and on current i, in both amplitude and polarity.

The "pumped" oxygen flow obeys Faraday's law and is given by the relation:

$$J = \frac{i}{4F} \quad (7)$$

in which J is expressed in molecules per hour, F and i having been defined hereinbefore.

As indicated hereinbefore, the invention proposes a sensor comprising two electrochemical cells. The first cell detects the stoichiometry of a small volume of gaseous mixture passes to it after catalysis, said small gaseous mixture volume coming from an "assay". The second cell is an ionic pump and modifies the composition of the gaseous mixture introduced into the sensor in such a way that the output signal $V_{E1/E2}$ of the measuring cell has a dip for a different value of the stoichiometry of the gaseous mixture in the form in which it really appears at the input of the sensor (Mex).

Figure 4:
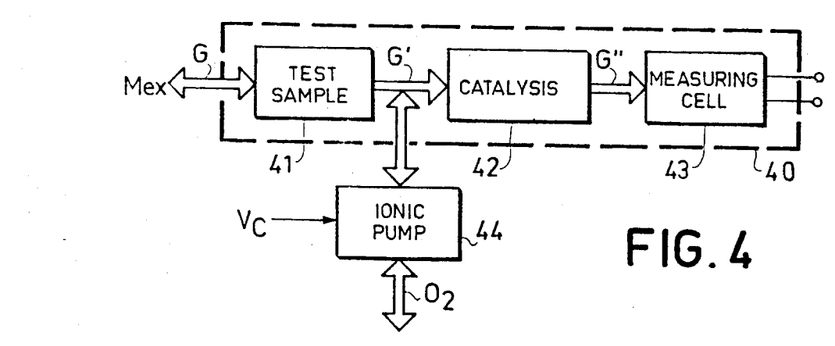
FIG. 4 a diagram illustrating the operation of a sensor according to the invention.

FIG. 4 diagrammatically illustrates the operation of a sensor according to the invention. Under reference 40 appear the three functions common to the prior art sensors, e.g. the sensors described relative to FIG. 1 and namely assay 41, catalysis 42 and measuring cell 43, said functions being wholly or partly realized by a common member. The composition of the gaseous mixture G' after each assay is, according to the prior art, identical or very close to the composition of the gaseous mixture in the external medium Mex in which circulates the mixtures to be measured. Prior to measurement, the gaseous mixture G'' is proved by relation (4). The ionic pumping cell 44, by means of a control voltage $V_c$ makes it possible to continuously modify the composition of the admitted gaseous mixture G' by injecting or removing oxygen. As is known, the assay function can be carried out in different ways, i.e. by means of a metering port, an inert porous body or, in the case of sensors like that of FIG. 1, by means of the actual catalyst body Ct extending the measuring electrode $E_2$. In reality, these functions correspond to regions of the sensor which, in general, cannot be distinguished as precisely and a single member may in itself carry out all or part of these functions. Ionic pumping can take place at any point between the measuring cell and the assay area, i.e. usually in the catalysis area.

The latter construction is particularly interesting because it simultaneously permits a good measuring sensitivity and a low admitted gas quantity, approximately 1 mm$^3$/s and e.g. between 0.5 and 5 mm$^3$/s. This is in addition to the technical advantages resulting from the use of thick or thin layer construction procedures. It is therefore possible to significantly modify the oxygen composition of the admitted mixture G' within the sensor without requiring a high ionic current within the solid electrolyte of the ionic pumping cell, i.e. the control voltage $V_c$ or, and this amounts to the same thing, current i.

It is also more advantageous to use a current source for producing control voltage i. Thus, if the cell is controlled by a voltage, the current passing through it is dependent on the temperature and as can be clearly gathered from relation (6). As the transferred ion quantity is directly proportional to the current, it is important that it is the current which is imposed and not the potential difference if the temperature is liable to vary or if no temperature regulation measures are taken. Unless indicated to the contrary, it will be considered hereinafter that the electric power supply controlling the ionic pumping cell is a current source.

Figure 5:
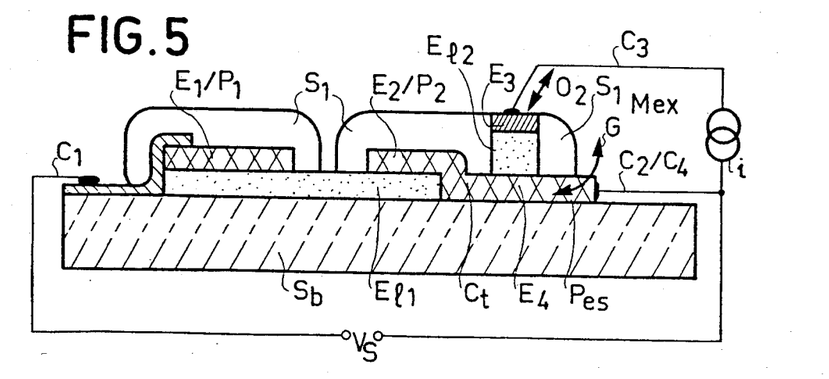
FIG. 5 a further embodiment of the sensor according to the invention in a first approach.

FIG. 5 is a sectional view of a first embodiment of sensors according to the invention and in accordance with a first approach.

The components which also occur in the prior art and which have been illustrated relative to FIG. 1 are again present, i.e. measuring cell $E_1/P_1 - E_{l1} - E_2P_2$ deposited in the form of thick or thin layers on a substrate $S_b$, catalysis region Ct and assay region $P_{es}$, where the interactions take place with mixture G circulating in the medium to be analysed. In the present embodiment, the two latter regions are in fact constituted by an extension of measuring electrode $E_2/P_2$. The output signals $V_S$ of the sensor is transmitted to external, not shown circuits by connections $C_1$ and $C_2$. At least the two electrodes $E_1/P_1$ and $E_2/P_2$ must be protected by a tight, inert insulating envelope $S_1$, e.g. of enamel.

According to the invention, a supplementary electrochemical cell is integrated into the sensor and comprises a solid electrolyte $E_{l2}$ inserted between two electrodes $E_3$ and $E_4$. In the embodiment of FIG. 5 and according to the first approach, the second electrode $E_4$ coincides with the extension of measuring electrode $E_2$. The assembly fills a channel made in the insulating envelope. The cell is flush with the surface of insulant $S_1$, so that it is linked with an oxygen-containing medium, which can be medium Mex in which circulates the gaseous mixture to be analysed G. Cell $E_3-E_{l2}-E_4$ is energised by a control current i via connections $C_3$ and $C_4$, $C_4$ coinciding with $C_2$.

If reference is again made to the description given relative to FIG. 4, it will immediately be apparent that the cell $E_3-E_{l2}-E_4$ functioning an an ionic pump modifies, as a function of the amplitude and the polarity of current i, the composition of the assay introduced into the sensor, i.e. the composition of the gaseous mixture circulating towards the catalysis region Ct and finally reaching measuring cell $E_2/P_2-E_{l1}-E_1/P_1$. Thus, the cell produces an output signal $V_S$ which no longer dips when the stoichiometry of the mixture G is reached and instead dips "before" or "after" the said stoichiometry, the displacement on either side of the latter being determined continuously by the amplitude and polarity of control current i.

Figure 6:
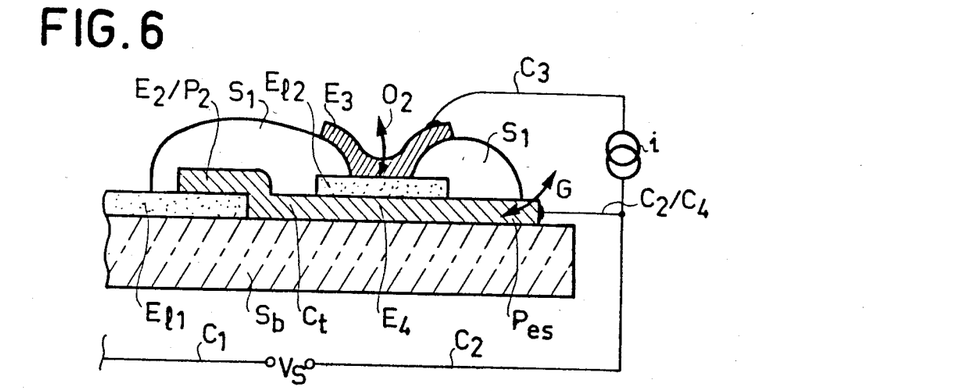
FIGS. 6 to 10 other embodiments according to this approach.

FIGS. 6 to 10 show other variants of constructions or construction processes of sensors according to the invention in accordance with the first approach. FIG. 6 shows a practical embodiment in which electrolyte $E_{l2}$ is in the form of a layer or wafer joined or deposited on the extension of the measuring electrode. The enamel coating is deposited last. The opening exposing electrolyte $E_{l2}$ can be produced by masking and electrode $E_3$ is then deposited. The latter electrode can also be produced by means of a platinum varnish.

The components which are common to those of FIG. 5 will not be described again. This also applies to the drawings to be described hereinafter.

Figure 7:
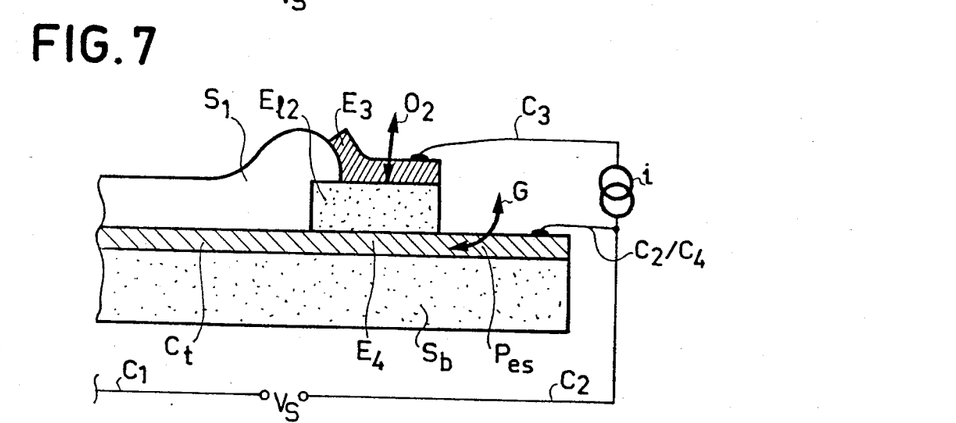
Figure 8:
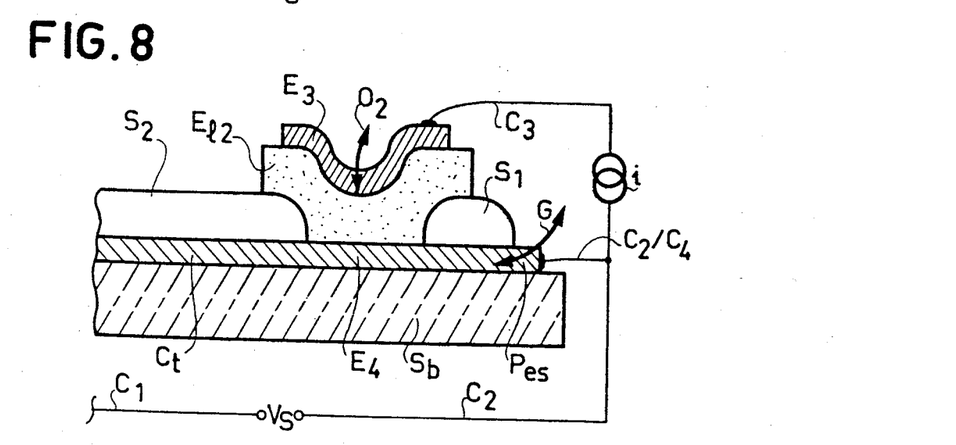

No problems result from the positioning of the electrolyte at the end of the substrate close to the assay region $P_{es}$ in the manner illustrated in FIG. 7. This arrangement obviates the need for an opening in enamel coating $S_1$. The electrolyte can also be in the form of a screen process printed coating in the manner illustrated in FIG. 8.

Figure 9:
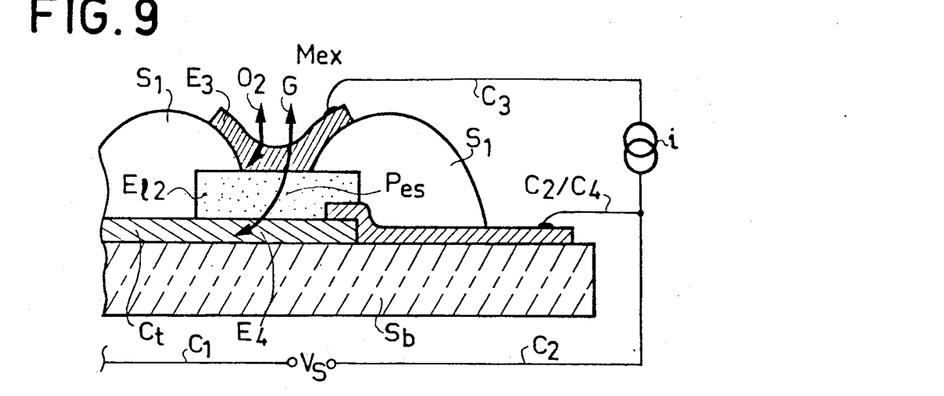
Figure 10:
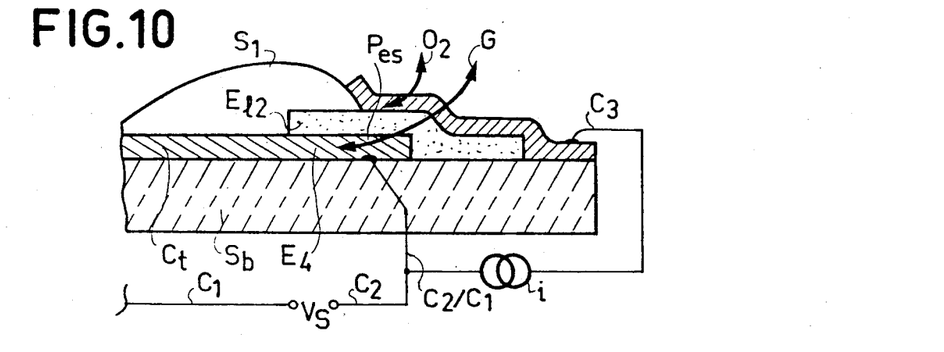

Finally, it is also possible for identity to exist between the assay and ionic pumping regions, as illustrated in FIGS. 9 and 10, by making electrode $E_3$ permeable to the gaseous mixture G and the solid electrolyte layer $E_{l2}$ must also have a limited thickness and be permeable. FIG. 10 more specifically illustrates the case where the electrolyte is deposited by screen process printing as in the case of FIG. 8.

From what has been described hereinbefore, electrode $E_4$ was identical with the extension of the measuring electrode. According to a second approach, whereof three variants are illustrated relative to FIGS. 11 to 13, electrode $E_4$ can be separate and the ionic pumping cell $E_3-E_{l2}-E_4$ is in the form of an element joined to the protective enamel $S_1$.

Figure 11:
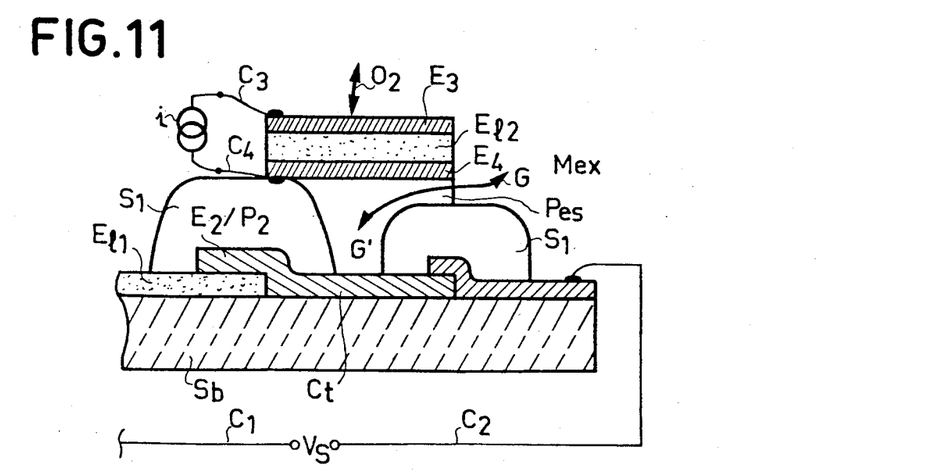
FIGS. 11 to 13 embodiments according to a second approach.

According to the first variant shown in FIG. 11 the assay region $P_{es}$ is in the form of a metering hole, as used in certain prior art sensor constructions. This leads to a predetermined limitation of the gaseous mixture quantity induced into the sensor, i.e. into an enclosure below the ionic pumping cell in which the composition of the gaseous mixture is modified and becomes G', due to the action of said cell. This enclosure can be produced at the time of manufacture and masking and depositing the enamel layer or by any other process. Cell $E_3-E_{l2}-E_4$ is then joined to the assembly.

Figure 12:
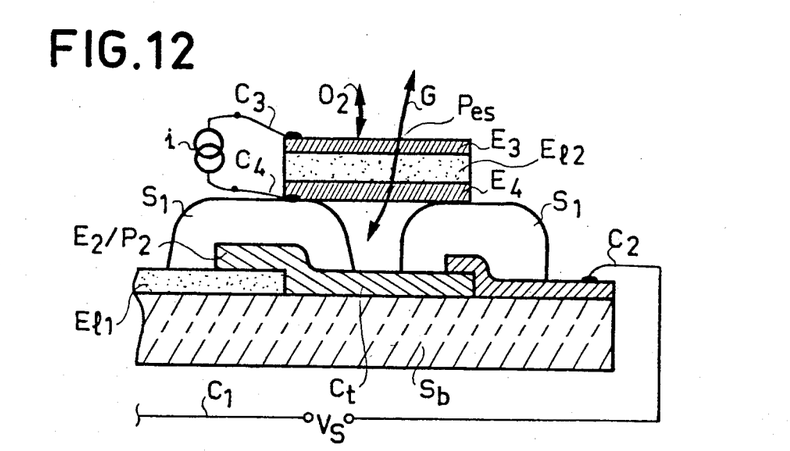

In FIG. 12, cell $E_3-E_{l2}-E_4$ also coincides with the assay region $P_{es}$, as for the variants of FIGS. 9 and 10 in the first approach.

Figure 13:
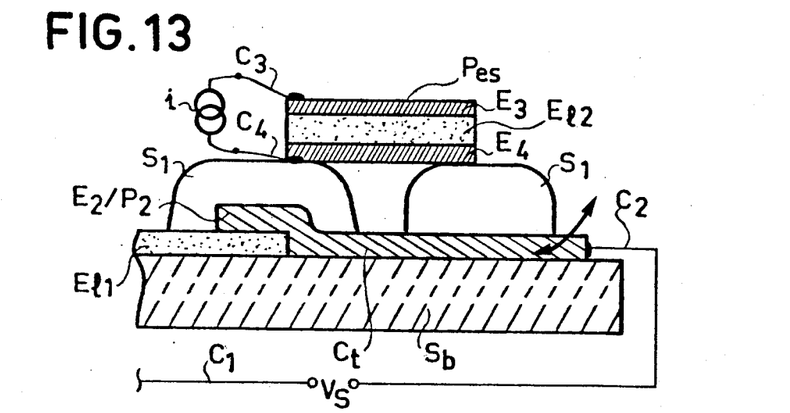

In FIG. 13, the assay region $P_{es}$ is separate from cell $E_3-E_{l2}-E_4$ and is produced in the same way as in the variants illustrated by FIGS. 5 to 8.

Figure 14:
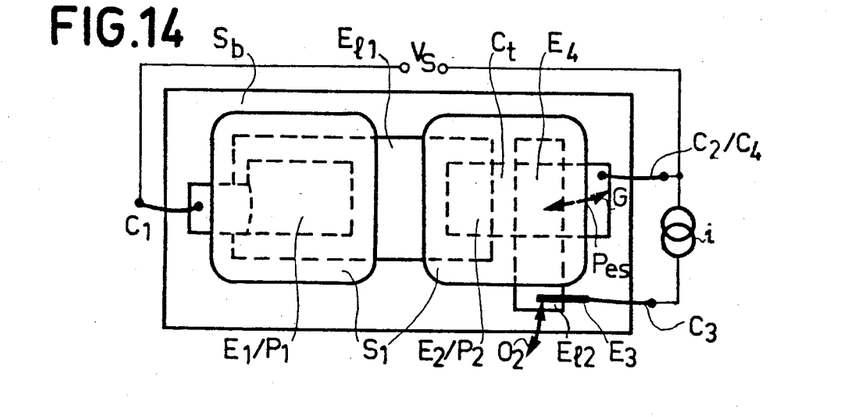
FIG. 14 an embodiment according to a third approach.

According to third approach illustrated in FIG. 14 in the form of a plan view, the ionic pumping cell $E_3-E_{l2}-E_4$ can be constructed in the same way as the measuring cell and have an overall planar structure instead of being in the form of a vertical stack, i.e. electrode-electrolyte-electrode. Electrolyte $E_{l2}$ is extended outwards, passing out of the enamel protective layer $S_1$. Electrode $E_3$ defines a useful exchange area with the oxygen present in the external medium and serves as a socket $C_3$.

A cell constructed in this way can also be adapted to the second approach. A second electrode is then deposited on the electrolyte, the assembly being joined or deposited on the insulating envelope. The second electrode is placed on the communication channel with the catalysis region of the measuring cell.

One of the most interesting uses for electrochemical sensors is in systems for regulating the richness of an air-fuel mixture introduced into an internal combustion engine. According to the prior art, the sensors are inserted in the exhaust pipes and are used for detecting the stoichiometry or a fixed value close thereto in the said pipes, i.e. relative to the exhaust gases. Electronic threshold circuits detect the dip of the curve at $\lambda_s$ (FIG. 2) and feedback loops act on the air-fuel mixture admission members for bringing about these conditions. The disadvantage of such regulation systems is that they can only define one regulation point.

The sensors according to the invention make it possible to displace the dip of the response curve "before" or "after" the true stoichiometry of the gaseous mixture circulating in the exhaust pipe in a continuous manner, and are of particular interest within the scope of the said application.

Figure 15:
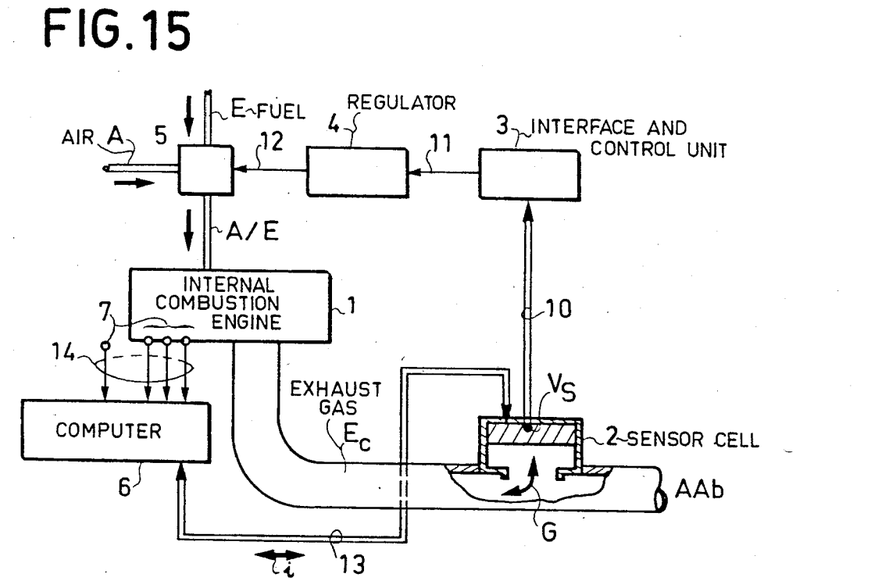
FIGS. 15 and 16 a regulating system in which the sensors according to the invention are used and the operation thereof.
Figure 16:
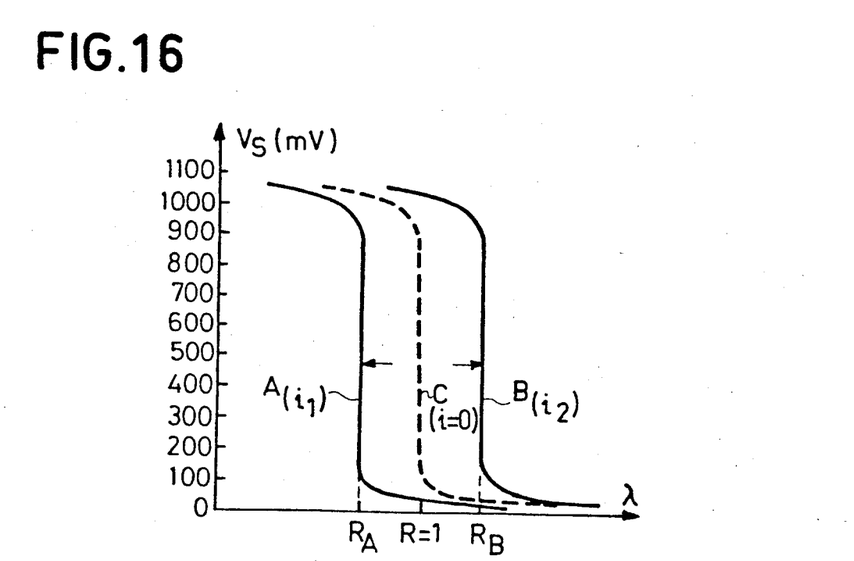

FIGS. 15 and 16 diagrammatically illustrate the use of the sensors according to the invention in a system for regulating the richness of an air-fuel mixture admitted into the cylinders of an internal combustion engine. Engine 1 has an intake for air A and fuel E, which are mixed in mixer 5. The latter can be a chamber carburettor, an injection device or any similar device. The mixture is supplied to engine 1 by pipe A/E. Mixer 5 is controlled by a regulator 4. The connection 12 is, for example, a mechanical coupling shaft. The burnt gases are then discharged into the atmosphere AAb by an exhaust pipe $E_c$. Sensor 2 according to the invention is positioned in the gas discharge path and communicates with the exhaust gases G. As shown in FIG. 15, the sensor is actually place in a box inserted in the exhaust pipe and is secured by any appropriate fixing means. This box provides a protection against the direct action of the exhaust gases. Only a sample of the exhaust gases or "assay" is admitted into the sensor 2, as stated hereinbefore. The electric output signal of measuring cell $V_S$ is transmitted to a control device 3 by electrical connections 10. The control device must be able to detect, e.g. by means of a threshold logic, the dip of curve $V_{E1/E2}$ and its output controls the regulating member 4 by connection 11.

If an automatic regulation is required, the regulating system is completed by an analog or digital computer 6 receiving from the various sensors 5 or control members 7 via connections 14 data relating to the characteristic operating parameters of the engine, as well as the environment and various instructions. As a non-limitative example, these parameters can be the external temperature, air flow range or engine operating conditions, i.e. acceleration, deceleration, etc. In addition to functions which are well known to the Expert, such as the processing of electric pulses transmitted to the spark plugs and which fall outside the scope of the invention, by means of special members the computer 6 generates the current i used for the control of the ionic pumping cell equipping the sensor 2 according to the invention, said current being transmitted by electric connections 13.

The amplitude and polarity of current i are used for determining the quantity of pumped, injected or extracted oxygen for the purpose of modifying the assay composition and consequently displacing the dip of the sensor response curve relative to the stoichiometry of the gaseous mixtures circulating in exhaust pipes $E_c$. Due to the retroaction or feedback effect caused by members 3 to 5, the air-fuel mixture introduced into pipe A/E is consequently modified.

FIG. 16 illustrates the operating cases of the regulating system of FIG. 15 for a given exhaust gas temperature.

If i=0, everything takes place as if the ionic cell did not exist. The composition of the gaseous mixture admitted into the sensor is not modified compared with that of the medium to be analysed. This case is illustrated by curve C and is the case when the prior art sensors, the dip taking place at the stoichiometry of the mixture circulating in the exhaust pipes. This case is defined as corresponding to a richness R of the mixture introduced into pipe A/E, R=1. A lean mixture is defined as having an air excess and a rich mixture as having a fuel excess.

Curves A and B correspond to values of control circuit i, respectively $i_1$ and $i_2$ such that the relation $|i_1| = -|i_2|$ is proved. In both cases, the dip of response curve $V_s$ of the sensor takes place when the measuring cell equipping the sensor detects the stoichiometry of the gaseous mixtures as transmitted to the measuring electrode and whereof the oxygen content has been modified in one or other direction by the ionic pumping cell after admission into the sensor ("assay").

The dip points are $R_A$ (lean mixture) and $R_B$ (rich mixture) and correspond to displacements of the same amplitude, but opposite direction compared with the stoichiometry. With the knowledge of the control current i, the richness of the air-fuel mixture admitted into the engine cylinders can be determined on detecting the dip of the curve. It is pointed out that this dip corresponds to the stoichiometry of the mixture admitted into the sensor at the measuring electrode.

Thus, the relationship between the control current i and the displacement amplitude of the curve dip relative to the true stoichiometry of the gaseous mixture at the sensor input, can be determined on the basis of experience or by calculation, notably by using relations (6) and (7), the quantity of fluid admitted into the sensor per unit of time being known ("assay"). As has been stated hereinbefore, a typical value is 1 $mm^3/s$ in the case of sensors similar to that described relative to FIG. 5.

The richness of the air-fuel mixture admitted into the cylinders can therefore be regulated about a continuously regulatable reference value by acting on the amplitude and polarity of the control current i, which in turn determines the "pumped" oxygen quantity. To this end, computer 6 incorporates a power supply, whose amplitude and polarity can be regulated or programmed (not shown in FIG. 15). Such regulatable sources or supplies are known to the expert and do not require a more detailed explanation here. The same applies regarding the exact processing conditions for current i and the curves relating to the variation in the richness of the mixture admitted as a result thereof. These curves are in particular dependent on the type of engine used.

Furthermore, this method is not limited to the regulation of the air-fuel mixture of an internal combustion engine. Without changing anything in the structure of the diagram of FIG. 11, engine 1 can be replaced as a non-limitative embodiment by the burners of a boiler. Sensor 2 is then placed in the burnt gas discharge circuit $E_c$. It can be applied to any apparatus having a combustion effect and the regulating action can be carried out in a non-automatic manner by modifying current i by means of a member for the manual control of the power supply.

A supplementary arrangement can be adopted for ensuring a better operation of the sensor according to the invention and this consists of regulating the sensor temperature to a predetermined value.

This arrangement can be adopted for a number of reasons. Firstly, it may be wished to control the ionic pumping cell by a voltage source. However, according to relations (6) and (7), the ionic current (and the quantity of the pumped chemical species) is dependent on the absolute temperature T when the control signal is produced by a voltage source. Secondly, and without this being limitative, at low temperature the ionic conductivity of solid electrolytes is very low, so that when the fluid to be measured is at low temperature, it is advantageous to heat the body of the sensor and keep it at a higher value.

Figure 17:
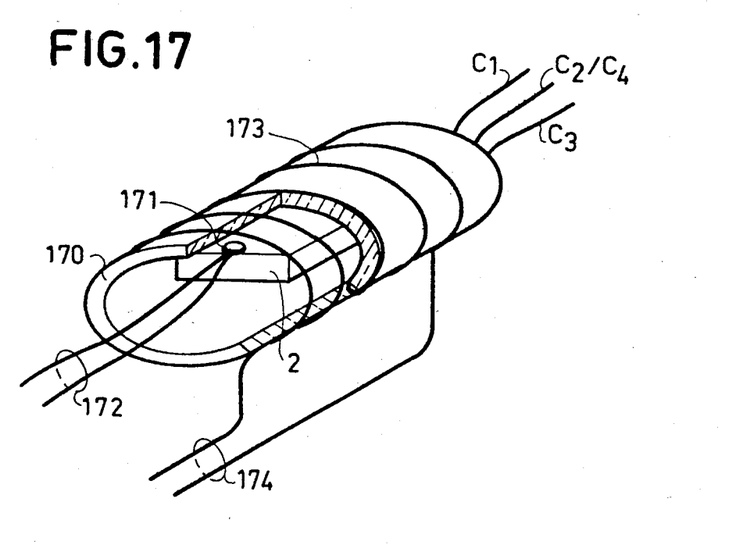
FIG. 17 an improvement which can be made to the sensors according to the invention.

Various devices are known for carrying out such a regulation. FIG. 17 illustrates the embodiment of such a device. The sensor 2 of FIG. 15 is inserted in an e.g. quartz tube 170. The assembly is surrounded by a resistance coil 173 supplied with an electric current by connections 174. This current can be fixed once and for all for ensuring an average temperature within the tube or conversely can be regulatable as a function of the temperature of the body of the sensor measured by a sensor 171, e.g. in the form of a thermocouple. The output signal of thermocouple 171 is transmitted via connections 172 to a not shown control device. Conventionally, this signal is compared with a reference value so as to adjust the current supplying the resistance heating coil 173 to a value compensating variations in the measured temperature.

The device described hereinbefore can be adapted to the sensors in accordance with all the aforementioned variants and can be used within the scope of the regulating system described relative to FIGS. 15 and 16. In this application, when the computer 6 is of the digital type, it is then necessary to provide a digital-analog converter to transform the digital signals processed by the computer into an analog control signal at current source i, said signal having a variable amplitude.

According to a fourth approach, the invention proposes a sensor construction making it possible to obviate this disadvantage.

Figure 18:
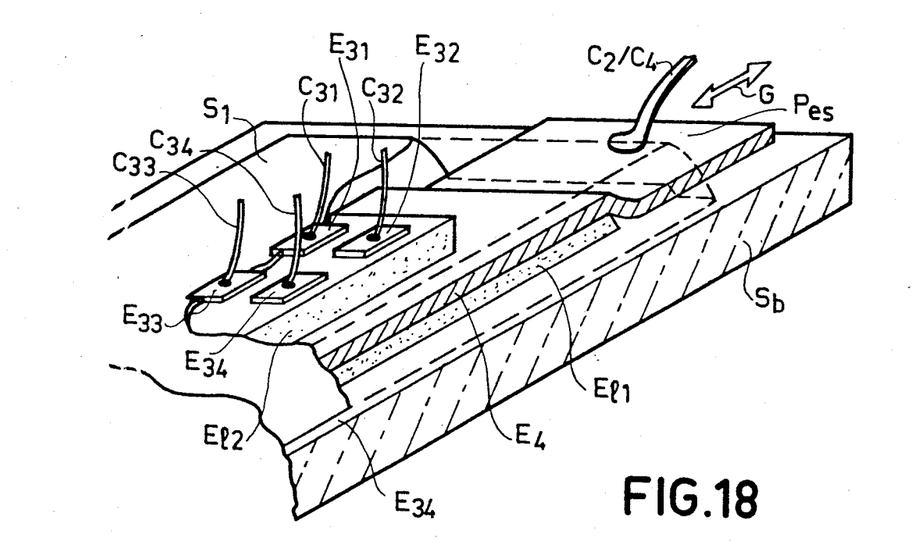
FIGS. 18 and 19 two embodiments of sensors according to the invention in a third approach.

A first embodiment of the sensor according to this approach is illustrated in the partial view of FIG. 18 in which portions have been cut away to show the hidden parts of the sensor. According to this approach, several pumping cells are integrated into the sensor. In the embodiment of FIG. 18, these cells have a common electrolyte $E_{l2}$ and a common electrode $E_4$, which is the extension of the measuring electrode of the measuring cell in the same way as in structures described hereinbefore. From the overall standpoint, the construction of the sensor of FIG. 18 is like that of the sensor described relative to FIG. 5 and the components not required for the understanding of the present approach will not be described again.

The individual ionic pumping cells are defined by the regions below electrodes $E_{31}$ to $E_{34}$, which are flush with the surface of insulant $S_1$ and on which electric contacts are formed with electric connections $C_{31}$ to $C_{33}$. In a more general manner, although four cells are shown in FIG. 18, their number can be random n.

If each of the electrodes can be traversed by an elementary current which can assume values o, $+\Delta i$ or $-\Delta i$, the equivalent control current i can assume any discrete value between 0 and $n\Delta i$ in absolute values. This leads to a total ionic current $J_t$ which, on the basis of relation (7) satisfies relation:

$$0 \leq |J_t| \leq \frac{n}{4F} i \quad (8)$$

The displacement amplitude of the dip of the response curve of measuring cells $E_1/P_1-E_{l1}-E_2/P_2$ on either side of the stoichiometry of the gaseous mixture at the sensor input can assume as may discrete values as there are ionic pumping cells equally equipping the sensor.

Figure 19:
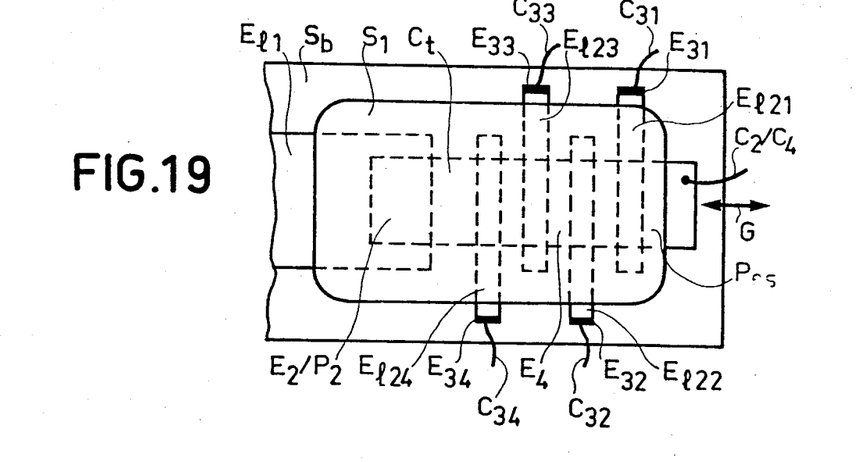

All the constructional variants described relative to FIGS. 5 to 14 can be used within the scope of the present approach. In particular, the construction described relative to FIG. 14 is of interest in the scope of the present approach. The adaptation of this construction is illustrated by FIG. 19.

Electrode $E_4$ is still common to all the cells, but the solid electrolyte is subdivided into elementary tongues $E_{l21}$ to $E_{l24}$ deposited on electrode $E_4$, which is an extension of measuring electrode $E_2/P_2$ and project gradually, e.g. in alternating manner over the two edges of substrate $S_b$. Electrodes $E_{31}$ to $E_{33}$ are peripherally deposited and ensure electric contact with connections $C_{31}$ to $C_{34}$.

As for the previous approaches, control of the ionic pumping cells can take place in voltage or in current. In the latter case, it is merely necessary to provide a set of n elementary bipolar current sources functioning on an "all or nothing" basis under the control of signals supplied by computer 6. When the ionic pumping cells are controlled in voltage, two types of arrangement are possible. The first consists of regulating the operating temperature of the sensor, for which purpose the device described relative to FIG. 17 can be used. The second consists of providing electrodes $E_{31}$ to $E_{34}$ with the same surface dimensions. If reference is again made to relation (5), it should be noted that impedance $Z_{el}$, which as a first approximation can be reduced to a resistance, $R_{el}$, is given by the relation:

$$Z_{el} = R_{el} = \frac{k}{\sigma A} \quad (9)$$

in which k is a proportionality constant

A the surface of the cell and $\sigma$ the ionic conductivity of the electrolyte, which is dependent on the temperature.

If the control voltage is the same for all the ionic pumping cells: "$E_{31}-E_{l2}-E_4$" to "$E_{34}-E_{l2}-E_4$", it follows that the elementary current traversing each cell is the same if the surfaces of electrodes $E_{31}$ to $E_{34}$ are identical. It is accepted that elecrolyte $E_{l2}$ is common to the cells or, if this is not the case, that $\sigma$ has the same value.

Figure 20:
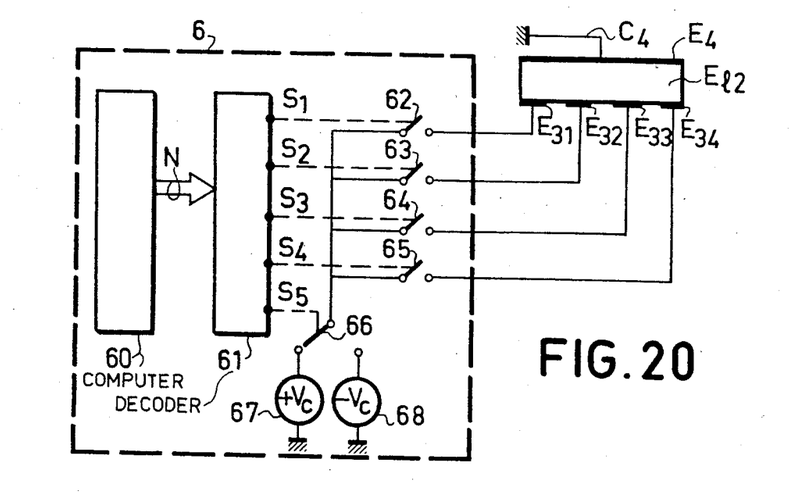
FIG. 20 diagrammatically, the use of a sensor in a regulation system.

FIG. 20 diagrammatically illustrates a voltage control circuit for the elementary ionic pumping cells of a sensor according to the fourth approach in connection with the regulating system of FIG. 15.

Computer 6 comprises an arithmetic element 60, which processes a control word N, e.g. in pure binary code transmitted to an interface and decoding circuit 61 supplying at outputs $S_1$ to $S_4$ five binary control signals, each of which actuates a switch 62 to 66 respectively. Switch 66 serves to put into operation a source 67 of positive control voltage $+V_c$ or a source 68 of negative control voltage $-V_c$, as a function of the desired displacement direction. The displacement amplitude is determined by the number of closed switches 62 to 65. These switches are in each case connected to one of the electrodes $E_{31}$ to $E_{34}$ defining the elementary ionic pumping cells. The common electrode $E_4$ is connected to the point common to the two sources 67, 68 at connection $C_4$. The number of bits of control word N is determined by the number of different logic states to be ensured at the output from the interface and decoding circuit 61, i.e. $(2n+1)\Delta i$, n being the number of electrodes. If $\Delta i$ is the current in each elementary cell resulting from the application of the voltage $\pm V_c$ the logic states are o, $+\Delta i, \ldots +n\Delta i, -\Delta i, \ldots -n\Delta i$ in the chosen example $2n+1=9$ and if n is expressed in pure binary, 5 bites are required leading to 16 possible states, certain of which will not be used.

Instead of imposing a constant value in each cell, it is possible to directly weight these currents: $\Delta i, 2\Delta i, 4\Delta i, 8\Delta i$ etc and directly use a binary control word.

In a supplementary variant, 2 ionic pumping cells can be used for obtaining currents $+\Delta i$ and $-\Delta i$ if the use of bipolar sources is not desired.

Figure 21:
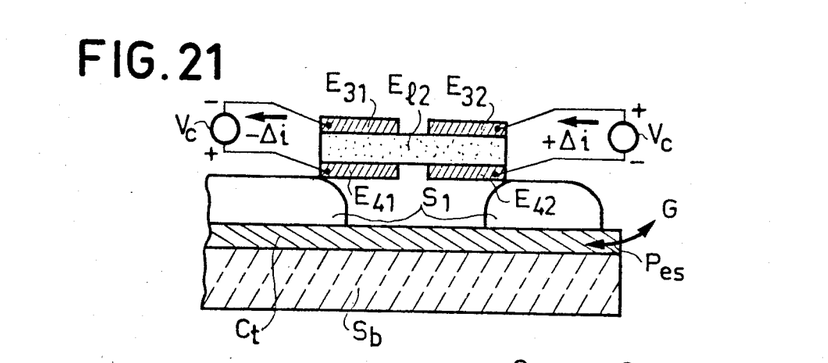
FIG. 21 a variant made to the construction of a sensor according to the fourth approach.

FIG. 21 diagrammatically illustrates this possibility. According to this variant, each elementary cell must have a pair of separate electrodes, namely $E_{31}-E_{34}$ and $E_{32}-E_{42}$. For this purpose, the structures described relative to FIGS. 11 to 14 are used. On connecting electrodes $E_{41}$ and $E_{32}$ to a potential $+V_c$ supplied by the control source via not shown switches and if electrodes $E_{31}$ and $E_{42}$ are applied to a potential OV, it follows that the two elementary cells $E_{31}-E_{l2}-E_{41}$ and $E_{32}-E_{l2}-E_{42}$ can be traversed by currents $-\Delta i$ and $+\Delta i$ respectively, leading to a displacement of the dip point of the response curve of the measuring cell $E_1/P_1-E_{l1}-E_2/P_2$, not shown in FIG. 21, of the same amplitude but opposite direction. In general, the number of cells is equal to 2n.

Naturally, this variant can also be adapted to the case where two ionic pumping cells are controlled in a similar manner by a current or voltage of variable amplitude, but a single polarity.

The operating case illustrated by FIG. 16 applies to an identical current alternately in the first and second cells, so that a displacement of the same amplitude but opposite direction is obtained (curves A and B).

Although the invention is not limited to the case of sensors produced according to the thin or thick layer method, they may be preferred for certain applications because they have a lower response inertia, reduced overall dimensions and can be produced by processes normally used in microelectronics. On the basis of the latter aspect, they can be closely associated with other electronic components produced on the same or an adjacent substrate protected from high temperaturs, so that the electronic circuits can function correctly. For example, connections $C_1/C_2$, which are also produced by deposition, can be connected to a threshold amplifier for detecting the dip of the curve in FIG. 2. However, this falls outside the scope of the invention. Other advantages have been defined in the aforementioned European Patent Application.

The invention is not limited to the embodiments described hereinbefore and in particular the technological environment of the external geometry, fixing method, electric contacts, etc has only been described in an illustrative manner. As is known, the different constituents of the sensor can be chosen from a wide range of materials and, in non-limitative manner, examples are given below:

Electrode $E_1/P_1$ can be formed from one of the following combinations: Ni/NiO, Pb/PbO, Ag/AgO, Pd/PdO or Cr/Cr$_2$O$_3$ or more generally by a system comprising a metal and a combination thereof with an element of column VI A of the periodic table.

Electrodes $E_2/P_2$, $E_3$ and $E_4$ can be made from platinum, silver or an alloy based on these metals.

Electrolytes $E_{l1}$ and $E_{l2}$ can be of zirconium dioxide, thoria or ceric oxide, stabilized by one or more elements of columns $II_A$ and $III_B$ of the periodic table, in the form of thick or thin layers or in solid form.

Catalyst $C_t$, if separate from the measuring electrode, can be made from platinum with a compact or porous texture, or can be constituted by an inert porous material such as zirconium dioxide or alumina filled with catalyst, metal or metallic oxide such as ZnO, CeO$_2$, MnO$_2$, Mn$_2$O$_3$, Co$_2$—O$_3$, NiO, CuO, Cu$_2$O$_3$, TiO$_2$, V$_2$O$_5$, Ag$_2$O or PbO.

The limitation means ensuring the assay can be constituted by an inert porous material such as zirconium dioxide or alumina.

The insulating materials can be constituted e.g. by dielectric enamels of the type conventionally used for the manufacturers of hybrid circuits or by other dielectric and inert layers deposited by thin or thick layer processes (adopting the procedure generally used in microelectronics).

The substrate can be of a good electrical insulant, which is inert to all the electrochemical reactions occurring during the operation of the sensor, but with a good mechanical behaviour and a good thermal adaptation. The best example is alumina in the form of a high quality ceramic or preferably monocrystalline alumina of the corundum or sapphire type. As a function of the operating temperature of the sensor, other materials can be used such as quartz, certain metal oxides in the ceramic or monocrystalline form or certain nitrides such as silicon nitride.

What is claimed is:

1. A solid electrolyte sensor for sensing the concentrations of reactive species contained in a fluid mixture comprising:

a primary cell including first, second and third regions, said first region having fluid flow limiting means for limiting the fluid flow introduced into said second region, said second region having catalysis means for bringing the admitted fluid into thermodynamic equilibrium, and said third region having an electrochemical measuring cell for detecting the stoichiometry of the reaction of said reactive species;

at least one supplementary electrochemical cell including first and second electrically-conducting means and solid electrolyte means, said solid electrolyte means operatively connected to and separating said first and second electrode means for permitting ionic conduction of one of the reactive species between said first and second electrode means;

electrical power source means operatively connected to said first and second electrode means for supplying an electrical current to said solid electrolyte means for establishing ionic conduction of the reactive species within the solid electrolyte means of predetermined amplitude and polarity;

said first electrode means being adapted to contact a medium supplying or receiving the reactive species or one of its components;

said second electrode means being operatively linked with the second region for modifying, in response to said ionic conduction, the relative concentrations of the fluid admitted into said second region by extraction or injection of the reactive species in a quantity proportional to the predetermined amplitude; and control means operatively connected to said power source means for controlling the supply of electric current to said first and second electrode means to selectively cause extraction or injection of the reactive species into said second region and for shifting the detected stoichiometry relative to a true stoichiometric value in response to the extraction or injection of the reactive species into said second region by virtue of said ionic conduction between said first and second electrode means.

2. A sensor according to claim 1, wherein the electrochemical measuring cell has a planar structure and comprises a first internal partial pressure reference electrode in partial or total contact by one of its faces with a solid electrolyte ionically conducting the reactive species and a second catalytic material electrode extending into the second region to form the catalysis means, said electrodes being covered by an inert protective envelope, which is tight to the species present in the fluid mixture and provided with a communication channel with the second region and in which the said supplementary electrochemical cell is in the form of a plate or wafer forming a solid electrolyte of a material which ionically conducts the said species covered on its two main faces respectively by the first and second electrodes, the plate or wafer being placed on the said envelope in such a way that the second electrode is in contact with the opening of the channel.

3. A sensor according to claim 2, wherein the means for limiting the flow introduced into the second region are constituted by an inert porous material.

4. A sensor according to claim 2, wherein the second and third regions are entirely filled with the catalyst material constituting the second electrode of the electrochemical measuring cell, the means for limiting the flow admitted into the second region being constituted by this material.

5. A sensor according to claim 2, wherein the supplementary electrochemical cell is made from porous materials permeable to the fluid mixture and constitutes the means for limiting the flow admitted into the second region.

6. A sensor according to claim 5, wherein the means for limiting the flow admitted into the second region are formed by an inert porous material.

7. A sensor according to claim 5, wherein the communication channel has a funnel shape and wherein the material forming the solid electrolyte and the first electrode of the supplementary electrochemical cell is in the form of layers of screen process printed materials.

8. A sensor according to claim 5, wherein the second and third regions are entirely filled with the catalyst material constituting the second electrode of the electrochemical measuring cell, the means for limiting the flow admitted into the second region being constituted by this material.

9. A sensor according to claim 5, wherein the supplementary electrochemical cell was made from porous material permeable to the fluid mixture and constitutes the means for limiting the flow admitted into the second region.

10. A sensor according to claim 2, wherein the said channel is also directly linked with the fluid mixture by a metering hole, which forms the means for limiting the flow of said fluid admitted into the second region.

11. A sensor according to claim 1, wherein the electrochemical measuring cell has a planar structure and comprises a first partial pressure internal reference electrode partly or totally in contact by one of its faces with a solid electrolyte which ionically conducts the reactive species and a second electrode made from catalytic material extending into the second region to form the catalysis means, the electrodes being covered by an inert protective envelope, which is tight to the species present in the fluid mixture and is provided with a communication channel with the second region and wherein the supplementary electrochemical cell comprises a solid electrolyte made from a material which ionically conducts the said species filling the channel and deposited on the extension of the second electrode of the measuring cell into the second region on which has been deposited an electrode of a conductive material whose surface is flush with the protective envelope, said electrode forming with the second electrode of the measuring cell respectively the first and second electrodes of the supplementary electrochemical cell.

12. A sensor according to claim 1, wherein the supplementary electrochemical cell comprises a solid electrolyte in the form of a thin wafer, which carries on one of its ends the first electrode in contact with a medium containing the reactive species and whose other end provided with the second electrode communicates with the second region, the ionic conductivity of the reactive species within the said wafer being in a direction parallel to its largest dimensions.

13. A sensor according to claim 1, wherein the reactive species is oxygen.

14. A sensor according to claim 13, wherein the solid electrolytes of the electrochemical measuring cell and the supplementary electrochemical cell are chosen from among the following materials: zirconium dioxide, thoria, ceric oxide doped with one or more elements of columns IIA and IIIB of the periodic table.

15. A sensor according to claim 13, wherein the electrodes of the electrochemical measuring cell and the supplementary electrochemical cell are comprised of platinum having a porous or compact texture or a porous inert material filled with platinum or metal oxides, the metals being chosen from among the following: titanium, vanadium, lead, silver, nickel, cobalt, chrome, copper, manganese, iron, cerium or zinc.

16. A system for regulating the richness of the air-fuel mixture of an internal combustion engine by electrochemical analysis of the exhaust gases containing oxygen comprising:

a solid electrolyte sensor means for sensing the concentration of oxygen in the exhaust gases and for generating an output signal representative of a stoichiometirc ratio of the air-fuel mixture, said sensor means including (a) a first cell having first, second and third regions, said first region having flow limiting means for limiting exhaust gas flow into said second region, said second region having catalysis means for bringing the admitted exhaust gas into thermodynamic equilibrium and said third region having at least one electrochemical measuring cell for detecting the stoichiometry of the reaction of the air-fuel mixture, and (b) at least one supplementary electrochemical cell including first and second electrically-conductive electrode means and solid electrolyte means, said solid electrolyte means being operatively connected to and separating said first and second electrode means for permitting ionic conduction of oxygen between said first and second electrode means;

electrical power source means operatively connected to said first and second electrode means for supplying an electrical current to said solid electrolyte means for establishing ionic conduction of the oxygen within said solid electrolyte means of predetermined amplitude and polarity, said first electrode means being adapted to contact said exhaust gases containing said oxygen and said second electrode means being operatively linked with the second region for modifying, in response to said ionic conduction, the relative concentrations of the exhaust gas admitted into said second region by extracting or injection of oxygen in a quantity proportional to said predetermined amplitude;

first control means operatively connected to said sensor means for receiving an output signal of said sensor means and for generating a control signal in response thereto;

regulator means connected to said first control means for receiving said control signal and for responsively regulating the stoichiometric ratio of the air-fuel mixture; and second control means for (1) controlling said electrical power means to selectively control the supply of electrical current to said first and second electrode means to cause selective extraction or injection of oxygen into said second region to thus establish said ionic conduction of oxygen within the solid electrolyte means as a direct function of the amplitude and polarity of the electric current supplied by said power source means and for (2) shifting the detected stoichiometric ratio relative to a true stoichiometric value in response to extraction or injection of oxygen into said second region by virtue of said ionic conduction between said first and second electrode means.

17. A system according to claim 16, wherein the sensor is associated with a temperature regulating device comprising a resistance heating coil traversed by a current controlled at a predetermined value and a control circuit incorporating a device for measuring the temperature controlling the current in this connection.

18. A system for regulating the richness of the air-fuel mixture of an internal combustion engine by electrochemical analysis of the exhaust gases containing oxygen comprising:

a solid electrolyte sensor means for sensing the concentration of oxygen in the exhaust gases and for generating an output signal representative of a stoichiometirc ratio of the air-fuel mixture, said sensor means including (a) a first cell having first, second and third regions, said first region having flow limiting means for limiting exhaust gas flow into said second region, said second region having catalysis means for bringing the admitted exhaust gas into thermodynamic equilibrium and said third region having at least one electrochemical measuring cell for detecting the stoichiometry of the reaction of the air-fuel mixture, and (b) at least one supplementary electrochemical cell including first and second electrically-conductive electrode means and solid electrolyte means, said solid electrolyte means being operatively connected to and separating said first and second electrode means for permitting ionic conduction of oxygen between said first and second electrode means;

electrical power source means including at least one of a voltage source and a current source operatively connected to said first and second electrode means for supplying an electrical current to said solid electrolyte means for establishing ionic conduction of the oxygen within said solid electrolyte means of predetermined amplitude and polarity, said first electrode means being adapted to contact said exhaust gases containing said oxygen and said second electrode means being operatively linked with the second region for modifying, in response to said ionic conduction, the relative concentrations of the exhaust gas admitted into said second region by extraction or injection of oxygen in a quantity proportional to said predetermined amplitude;

first control means operatively connected to said sensor means for receiving an output signal of said sensor means and for generating a control signal in response thereto;

regulator means connected to said first control means for receiving said control signal and for responsively regulating the stoichiometric ratio of the air-fuel mixture; and second control means including a digital or analog computer means for transmitting control signals to the electric power supply means and having means permitting selective programming of amplitude and plurality for (1) controlling said electrical power means to selectively control the supply of electrical current to said first and second electrode means to cause selective extraction or injection of oxygen into said second region to thus establish said ionic conduction of oxygen within the solid electrolyte means as a direct function of the amplitude and polarity of the electric current supplied by said power source means and for (2) shifting the detected stoichiometric ratio relative to a true stoichiometric value in response to extraction or injection of oxygen into said second region by virtue of said ionic conduction between said first and second electrode means.

19. A system for regulating the richness of the air-fuel mixture of an internal combustion engine by electrochemical analysis of the exhaust gases containing oxygen comprising:

a solid electrolyte sensor means for sensing the concentration of oxygen in the exhaust gases and for generating an output signal representative of a stoichiometric ratio of the air-fuel mixture, said sensor means including (a) a first cell having first, second and third regions, said first region having flow limiting means for limiting exhaust gas flow into said second region, said second region having catalysis means for bringing the admitted exhaust gas into thermodynamic equilibrium and said third region having at least one electrochemical measuring cell for detecting the stoichiometry of the reaction of the air-fuel mixture, and (b) a plurality of supplementary electrochemical cell including first and second electrically-conductive electrode means and solid electrolyte means, said solid electrolyte means being operatively connected to and separating said first and second electrode means for permitting ionic conduction of oxygen between said first and second electrode means;

electrical power source means operatively connected to said first and second electrode means of each of said plurality of supplementary electrochemical cells for supplying an electrical current to said respective solid electrolyte means for establishing ionic conduction of the oxygen within said solid electrolyte means of predetermined amplitude and polarity which is a direct function of the amplitude of the electric power supply means associated therewith, said first electrode means being adapted to contact said exhaust gases containing said oxygen and said second electrode means being operatively linked with the second region for modifying, in response to said ionic conduction, the relative concentrations of the exhaust gas admitted into said second region by extracting or injection of oxygen in a quantity proportional to said predetermined amplitude;

first control means operatively connected to said sensor means for receiving an output signal of said sensor means and for generating a control signal in response thereto;

regulator means connected to said first control means for receiving said control signal and for responsively regulating the stoichiometric ratio of the air-fuel mixture; and second control means for (1) controlling said electrical power means to selectively control the supply of electrical current to said first and second electrode means to cause selective extraction or injection of oxygen into said second region to thus establish said ionic conduction of oxygen within the solid electrolyte means as a direct function of the amplitude and polarity of the electric current supplied by said power source means and for (2) shifting the detected stoichiometric ratio relative to a true stoichiometric value in response to extraction or injection of oxygen into said second region by virtue of said ionic conduction between said first and second electrode means.

20. A system according to claim 19, wherein the second control means comprise a digital computer means for supplying binary output signals for controlling on an all or nothing basis the power supplies associated with the supplementary electrochemical cell means so as to activate a predetermined number thereof and cause an elementary ionic current of the same amplitude to traverse each activated cell means the instantaneous sum of these currents and their polarity determining the amplitude and direction of the variation of the relative concentrations of the reactive species present in the exhaust gases admitted into the second region, so as to define discrete variations of the richness regulation point.

21. A system according to claim 19, wherein the number of said supplementary electrochemical cells is an even number so as to be able to define first and second sets of cells and wherein the electric power supplies associated with these cells supply signals of a single polarity, the first electrodes of the cells of the first set being connected to the terminals of a first polarity of said electric power supply means and the second electrodes of the cells of the second set are connected to the terminals of the second polarity, the cells of respectively the first and second sets being alternately activated so as to define ionic currents of opposite directions.

* * * * *